(12) United States Patent
Zhou et al.

(10) Patent No.: US 10,995,175 B2
(45) Date of Patent: May 4, 2021

(54) THERMOPLASTIC POLYURETHANE MATERIALS FOR FORMING MEDICAL DEVICES

(71) Applicant: Becton, Dickinson and Company, Franklin Lakes, NJ (US)

(72) Inventors: Ming Zhou, Draper, UT (US); Theresa Hermel-Davidock, Newton, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 131 days.

(21) Appl. No.: 15/291,291

(22) Filed: Oct. 12, 2016

(65) Prior Publication Data

US 2017/0107320 A1    Apr. 20, 2017

Related U.S. Application Data

(60) Provisional application No. 62/241,339, filed on Oct. 14, 2015.

(51) Int. Cl.
| | | |
|---|---|---|
| *C08G 18/76* | (2006.01) | |
| *C08G 18/32* | (2006.01) | |
| *C08G 18/48* | (2006.01) | |
| *C08G 18/50* | (2006.01) | |
| *C08G 18/66* | (2006.01) | |
| *A61L 29/06* | (2006.01) | |
| *B29B 9/08* | (2006.01) | |
| *B29B 9/02* | (2006.01) | |
| *B29B 9/12* | (2006.01) | |
| *B29C 48/10* | (2019.01) | |
| *B29C 48/00* | (2019.01) | |
| *B29C 48/395* | (2019.01) | |
| *C08L 75/08* | (2006.01) | |
| *C08K 5/00* | (2006.01) | |
| *B29K 75/00* | (2006.01) | |
| *B29K 105/00* | (2006.01) | |
| *B29L 31/00* | (2006.01) | |
| *C08K 3/30* | (2006.01) | |

(52) U.S. Cl.
CPC .......... *C08G 18/7614* (2013.01); *A61L 29/06* (2013.01); *B29B 9/02* (2013.01); *B29B 9/08* (2013.01); *B29B 9/12* (2013.01); *B29C 48/022* (2019.02); *B29C 48/10* (2019.02); *B29C 48/397* (2019.02); *C08G 18/3206* (2013.01); *C08G 18/4854* (2013.01); *C08G 18/503* (2013.01); *C08G 18/5024* (2013.01); *C08G 18/6674* (2013.01); *C08G 18/6681* (2013.01); *C08G 18/7671* (2013.01); *C08K 5/0058* (2013.01); *C08L 75/08* (2013.01); *B29K 2075/00* (2013.01); *B29K 2105/253* (2013.01); *B29K 2995/0077* (2013.01); *B29L 2031/7542* (2013.01); *C08K 2003/3045* (2013.01)

(58) Field of Classification Search
CPC ............ C08G 18/7614; C08G 18/5024; C08G 18/6674; C08G 18/7671; C08G 18/6681; C08G 18/503; C08G 18/3206; C08G 18/4854; C08L 75/04; C08L 75/08; A61M 25/0009; A61M 25/00; B29B 9/02; B29B 9/08; B29B 9/12; B29C 47/385; B29C 47/0026; B29C 47/0004; B29C 48/10; B29C 48/022; B29C 48/397; A61L 29/06; C08K 2003/3045; C08K 5/0058; B29K 2075/00; B29K 2105/253; B29K 2995/0077; B29L 2031/7542
See application file for complete search history.

(56) References Cited

U.S. PATENT DOCUMENTS

| | | | |
|---|---|---|---|
| 4,058,506 A * | 11/1977 | Vaeth | C08G 18/10 528/65 |
| 4,935,480 A | 6/1990 | Zdrahala | |
| 4,939,007 A | 7/1990 | Hu | |
| 5,059,269 A | 10/1991 | Hu | |
| 5,061,254 A | 10/1991 | Karakelle | |
| 5,159,050 A | 10/1992 | Onwumere | |
| 5,159,051 A | 10/1992 | Onwumere | |
| 5,226,899 A | 7/1993 | Lee | |
| 5,250,649 A | 10/1993 | Onwumere | |
| 5,254,662 A | 10/1993 | Szycher | |
| 5,266,669 A | 11/1993 | Onwunaka | |
| 5,281,677 A | 1/1994 | Onwunaka | |

(Continued)

FOREIGN PATENT DOCUMENTS

| | | |
|---|---|---|
| EP | 2517828 A1 | 10/2012 |
| WO | 87/07155 A1 | 12/1987 |

OTHER PUBLICATIONS

PCT International Preliminary Report on Patentability in PCT/US2016/056738 dated Apr. 26, 2018, 9 pages.

(Continued)

*Primary Examiner* — Rabon A Sergent
(74) *Attorney, Agent, or Firm* — Servilla Whitney LLC

(57) ABSTRACT

Principles and embodiments of the present invention relate generally to thermoplastic polyurethane materials having controlled and improved stiffness and/or flexibility, and methods to prepare them. The thermoplastic polyurethanes described herein having superior stiffness and softening properties may be fabricated into film, tubing, and other forms of medical devices. The thermoplastic polyurethanes comprise: an aromatic diisocyanate excluding non-aromatic diisocyanates; at least one polyglycol; and a chain extender comprising at least one side-chain branching diol and excluding linear diols.

5 Claims, 1 Drawing Sheet

(56) References Cited

U.S. PATENT DOCUMENTS

| | | | |
|---|---|---|---|
| 5,545,708 A | 8/1996 | Onwunaka | |
| 2005/0025966 A1* | 2/2005 | Vedula | C08G 18/0895 |
| | | | 428/364 |
| 2005/0261427 A1* | 11/2005 | Saito | B32B 5/18 |
| | | | 525/88 |
| 2017/0334034 A1* | 11/2017 | Kadowaki | B24B 37/24 |

OTHER PUBLICATIONS

PCT International Search Report & Written Opinion issued for International Application No. PCT/US2016/056738, dated Jan. 25, 2017, 13 pgs.

* cited by examiner

THERMOPLASTIC POLYURETHANE MATERIALS FOR FORMING MEDICAL DEVICES

CROSS-REFERENCE TO RELATED APPLICATIONS

This application claims priority under 35 U.S.C. § 119(e) to U.S. Provisional Application No. 62/241,339, filed Oct. 14, 2015, the disclosures of which are incorporated herein by reference in their entirety.

TECHNICAL FIELD

Principles and embodiments of the present invention relate generally to thermoplastic polyurethane materials having controlled and improved stiffness and/or flexibility, and methods to prepare them. More particularly, the thermoplastic polyurethane materials are for forming medical devices.

BACKGROUND

Polyurethane thermoplastic materials are some of the most commonly used biomaterial polymer for various medical applications. For peripheral IV catheters, polyurethane is preferred to Teflon® for the catheter tubing. For peripherally inserted central catheter (PICCs) and central venous catheter (CVCs), most catheters are either made of silicone or polyurethane. However, one limitation of currently-available polyurethane catheter tubing is its incapability to achieve both high inherent stiffness at ambient conditions and flexibility after being exposed to liquids in the environment of the body.

Polyurethane thermoplastic materials have been recognized as biomaterial polymers for a long time, but many can suffer from two major drawbacks: (i) the stiffness and the flexibility are not controllable or poorly controlled; and (ii) they are not resistant to microbial colonization on the surface, which may lead to infection or other complication. This limits many types of polyurethane medical applications, especially for long-term medical uses. In some cases, these materials are not able to maintain their original stiffness or other physical property and their physical properties change too quickly.

For medication infusion or injection, an invasive medical device is typically used to create a fluid channel from a medication reservoir to the patient, usually to vascular vessels or subcutaneous tissue. To ensure success of insertion to the body tissue of a target area, the entry portion of the device needs to be stiff enough for minimum pain. Once reaching the tissue, such as a blood vessel, the part of the device that remains in the tissue needs to be soft enough to minimize potential complications, such as mechanical phlebitis. In some instances, a catheter may cause phlebitis, which is an inflammation of a vein, due to local trauma to the vein in which the catheter is inserted. Harder catheters in the vein can be more likely to cause such trauma.

Thermoplastic polyurethanes (TPPs) suitable for medical devices are typically synthesized from three basic components, a diisocyanate, a polyglycol, and a chain extender, usually a low molecular weight diol, diamine, or water. If the chain extender is a diol, the polyurethane consists entirely of urethane linkages. If the extender is water or diamine, both urethane and urea linkages are present, which results in a polyurethaneurea (PUU). Inclusion of an amine-terminated polyether to the polyurethane synthesis also results in a polyurethaneurea (PUU). Device applications for thermoplastic polyurethanes include peripheral and central venous catheters. Thermoplastic polyurethanes chain extended with diols used in medical devices are disclosed in the following co-owned patents: U.S. Pat. Nos. 5,545,708; 5,226,899; 5,281,649; and 5,266,669.

Polyurethane and polyurea chemistries are based on the reactions of isocyanates with other hydrogen-containing compounds, where isocyanates are compounds having one or more isocyanate group (—N=C=O). Isocyanate compounds can be reacted with water ($H_2O$), alcohols (R—OH), carboxylic acids (R—COOH), amines ($R_x$—$NH_{(3-x)}$), ureas (R—NH—$CONH_2$), and amides (R—$CONH_2$). Certain polyurethanes may be thermoplastic elastomers (TPE), whereas other compositions may be highly cross-linked.

Thermoplastic polyurethanes comprise two-phases or microdomains conventionally termed hard segments and soft segments, and as a result are often referred to as segmented polyurethanes. The hard segments, which are generally of high crystallinity, form by localization of the portions of the polymer molecules which include the diisocyanate and chain extender(s). The soft segments, which are generally either non-crystalline or of low crystallinity, form from the polyglycol or the optional amine-terminated polyether. The hard segment content is determined by the weight percent of diisocyanate and chain extender in the polyurethane composition, and the soft segment content is the weight percent of polyglycol or polydiamine. The thermoplastic polyurethanes may be partly crystalline and/or partly elastomeric depending on the ratio of hard to soft segments. One of the factors which determine the properties of the polymer is the ratio of hard and soft segments. In general, the hard segment contributes to hardness, tensile strength, impact resistance, stiffness and modulus while the soft segment contributes to water absorption, elongation, elasticity and softness.

Generally, stiff polyurethanes maintain relatively high stiffness even after soaking in liquid. Soft polyurethanes with superior flexibility in liquid usually do not have sufficient stiffness for insertion. Because of this hurdle, there has not yet been a solution that is capable of meeting both customer needs. Clinicians typically have to choose one property and sacrifice the other.

While significant improvement in catheter performance has resulted over time, there remains a need for a polyurethane having the blood compatibility necessary for catheter manufacture which is stiff when dry for catheter insertion but which becomes soft and pliable for positioning and indwelling. There also remains a need for a catheter having blood compatibility, which retains sufficient mechanical strength and stiffness for ease of insertion and repositioning if desired.

SUMMARY

Provided are thermoplastic polyurethanes that provide both high inherent stiffness of the polymer and flexibility after being exposed to liquids in the environment of the body.

Various embodiments are listed below. It will be understood that the embodiments listed below may be combined not only as listed below, but in other suitable combinations in accordance with the scope of the invention.

One aspect of the present invention is directed to a thermoplastic polyurethane comprising a reaction product of an aromatic diisocyanate; at least one polyglycol; and a chain extender comprising at least one side-chain branching diol and excluding linear diols, and optionally, an amine-terminated polyether; with the proviso that the polyurethane does not contain any non-aromatic diisocyanates, and wherein the polyurethane has an isocyanate index in the range of 1 to 1.4. In one or more embodiments, the side-chain branching diol has a structure according to Formula (IV):

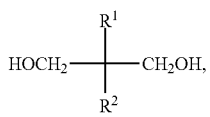

(IV)

where $R^1$ is a methyl group, and $R^2$ is a methyl group or hydrogen atom. In one or more embodiments, the side-chain branching diol comprises 2,2-dimethyl-1,3-propanediol, 2-methyl-1,3-propanediol, or both in a weight ratio of from 0:100 to 100:0 of 2,2-dimethyl-1,3-propanediol to 2-methyl-1,3-propanediol. In another embodiment, the polyurethane comprises only one side-chain branching diol as the chain extender. In a detailed embodiment, the side-chain branching diol consists essentially of a mixture of 2,2-dimethyl-1,3-propanediol and 2-methyl-1,3-propanediol in a weight ratio of from 10:90 to 90:10.

In one or more embodiments, the at least one polyglycol may be selected from the group consisting of polyethylene oxide glycol (PEG), polypropylene oxide glycol (PPG), polytetramethylene ether glycol (PTMEG), polyesterglycol, silicone glycol, polycarbonate glycol and combinations thereof. In a specific embodiment, where at least one polyglycol is polytetramethylene ether glycol (PTMEG) having the formula:

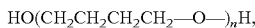

where n has an average value in the range of 3 to 40. In yet another embodiment, the at least one polyglycol is a blend of at least two or more PTMEGs, a first PTMEG having a first nominal molecular weight in the range of 250 to less than 1000 daltons and a second PTMEG having a second nominal molecular weight in the range of 1000 to 2900 daltons. In a specific embodiment, the at least one polyglycol is a blend of two or more of PTMEGs having varying molecular weights (MW): PTMEG250, PTMEG650, PTMEG1000, PTMEG1450, PTMEG1800, PTMEG2000, and PTMEG2900, where the number after "PTMEG" is a nominal MW in daltons. PTMEG250 has a MW=230-270, PTMEG650 has a MW=625-675, PTMEG1000 has a MW=950-1050, PTMEG1450 has a MW=1350-1450, PTMEG1800 has a MW=1700-1900, PTMEG2000 has a MW=1900-2100, and PTMEG2900 has a MW=2825-2975.

In one or more embodiments, the aromatic diisocyanate is selected from the group consisting of diphenylmethane-4,4'-diisocyanate (MDI), 2,4-toluene diisocyanate, 2,6-toluene diisocyanate (TDI), 1,5-naphthalene diisocyanate (NDI), 3,3'-dimethyldiphenyl 4,4'-diisocyanate (TODI), 4,6'-xylylene diisocyanate (XDI), 3,3'-dimethyl-diphenylmethane 4,4'-diisocyanate (DMMDI), dianisidine diisocyanate (DADI), and combinations thereof. In a specific embodiment, the aromatic diisocyanate is 4,4'-diphenylmethane diisocyanate, and has hard segment content between 50% and 75% by weight.

In one or more embodiments, the polyurethane is formed by a one-step bulk polymerization without a catalyst.

The thermoplastic polyurethane may further comprise one or more of a radiopaque material, an anti-thrombogenic agent, an antimicrobial agent, a lubricant, or a colorant.

In one or more embodiments, the side-chain branching diol chain extender comprises about 5% to about 20% (w/w) of the polyurethane.

In an embodiment, the thermoplastic polyurethane comprises the amine-terminated polyether, which is one or more amine-terminated polyethers having repeating units of ethylene oxide, propylene oxide, or tetramethylene oxide and having a molecular weight in the range of about 400 to 8,000.

Another aspect of the present invention is directed to a melt-processable thermoplastic polyurethane comprising the reaction product of: an aromatic diisocyanate selected from the group consisting of 4,4'-diphenylmethane diisocyanate, 2,2'-dimethyl-4,4'-biphenyldiisocyanate, 3,3'-dimethyl-4,4'-biphenyl diisocyanate, and combinations thereof; at least one polyglycol selected from the group consisting of polyethylene oxide glycol (PEG), polypropylene oxide glycol (PPG), polytetramethylene ether glycol (PTMEG), polyesterglycol, silicone glycol, polycarbonate glycol and combinations thereof; and at least one chain extender selected from the group consisting of 2,2-dimethyl-1,3-propanediol, 2-methyl-1,3-propanediol, and combinations thereof.

A detailed embodiment provides that the polyurethane comprises, in weight percentages based on the polyurethane: about 40 to about 55% of the aromatic diisocyanate; about 15 to about 59.9% of the at least one polyglycol; and about 0.1 to about 25% of the at least one chain extender, and optionally, 0 to about 30% of the amine-terminated polyether; with the proviso that the amounts add to 100%.

The melt-processable thermoplastic polyurethane may further comprise one or more of a radiopaque material, an antithrombogenic agent, an antimicrobial agent, a lubricant, or a colorant.

In one or more embodiments, the polyurethane has a hard segment content between 50% and 75% by weight. In one or more embodiments, the aromatic diisocyanate is present in an amount in the range of about 46 to about 49% (w/w) and the chain extender is present in an amount in the range of about 12 to about 18% (w/w) of the polyurethane.

In a specific embodiment, the chain extender consists essentially of a branched aliphatic diol selected from the group consisting of: 2-methyl-1,3-propanediol, 2,2-dimethyl-1,3-propanediol, 3-methyl-1,5-pentanediol. Preferably the branched aliphatic diols are saturated to avoid potential crosslinking reactions. In one or more embodiments, the branched aliphatic diols are di-substituted. In a more specific embodiment, the chain extender consists of 2,2-dimethyl-1,3-propanediol.

Yet another aspect of the present invention is directed to a vascular access device comprising the melt-processable thermoplastic polyurethane described herein. In one or more embodiments, the vascular access device may be a central venous catheter, a peripherally inserted central catheter, or peripheral intravenous cannula.

In a further aspect, a method of making a vascular access device comprises: combining the following ingredients: an aromatic diisocyanate excluding non-aromatic diisocyanates; at least one polyglycol; and a chain extender comprising at least one side-chain branching diol and excluding linear diols; polymerizing in the ingredients in a one-step bulk polymerization without a catalyst to form a thermoplastic polyurethane; curing the polyurethane; convening the polyurethane into chips suitable for melt forming; and melt forming the polyurethane into vascular access devices. The side-chain branching diol may consist essentially of 2,2-dimethyl-1,3-propanediol, 2-methyl-1,3-propanediol, or both in a weight ratio of from 0:100 to 100:0 of 2,2-dimethyl-1,3-propanediol to 2-methyl-1,3-propanediol.

DETAILED DESCRIPTION

Figure 1:
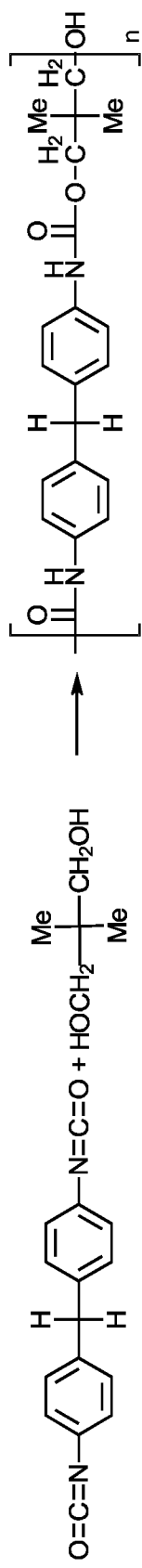
FIG. 1 illustrates an example of a polyurethane product produced by the reaction of an aromatic diisocyanate and a side-chain branching diol chain extender.

Before describing several exemplary embodiments of the invention, it is to be understood that the invention is not limited to the details of construction or process steps set forth in the following description. The invention is capable of other embodiments and of being practiced or being carried out in various ways.

The following terms shall have, for the purposes of this application, the respective meanings set forth below.

A polyglycol is a long chain (high molecular weight) polymer derived from an alkylene oxide containing ether-glycol linkages. Polyglycols include polyetherglycols.

A chain extender is a short chain (low molecular weight) hydroxyl- and/or amine-terminated compounds used during polymerization to impart desired properties to a polymer.

With respect to polyurethane chemistry:

$$\text{Isocyanate index} = \frac{\text{Isocyanate equivalents}}{\text{polyol equivalents}}$$

The isocyanate equivalent is defined as the weight of sample which will combine with 1 g equivalent weight of the aromatic diisocyanate. The sample is generally a polyol, amine or other compound that possesses groups capable of reacting with an isocyanate. See C. Hepburn "*Polyurethane Elastomers*" 2nd Edition, Springer, pages 42-43, (1992). In general, the polyurethane becomes harder with an increasing isocyanate index. There is, however, a point beyond which the hardness does not increase and the other physical properties begin to deteriorate.

Principles and embodiments of the present invention relate generally to polyurethane materials having controlled and improved stiffness and flexibility, and methods of preparing them.

Principles and embodiments of the present invention also relate generally to invasive medical devices used to create a fluid channel from a medication reservoir to a patient in need thereof, where the fluid channel may be inserted into and in fluid communication with vascular vessels, or subcutaneous tissue, where the invasive medical device comprises any of the polyurethane materials as described herein.

One or more embodiments relate to polyurethane materials that maintain both high stiffness in ambient conditions, and superior softening behavior after being soaked in a liquid, including body fluid in vivo.

One or more embodiments of the present invention relate to polyurethane polymers that can be used as raw material for catheter tubing via extrusion or molding, where the formed catheter tubing is capable of improving the success of insertion due to increased initial tubing stiffness, and/or significantly extending the catheter tubing's indwelling and reducing catheter tubing induced clinical complications because of its greater flexibility. In various embodiments, the catheter has a predetermined balance of stiffness for insertion and repositioning and pliability for threading through a blood vessel, where the catheter may comprise a polyurethane polymer described herein, and a radiopaque agent as a visualizing aid in placement and/or repositioning of the catheter.

Stiffness, flexibility and polyurethane's capability of softening in response to environmental changes depend on the polyurethane's molecular structure and polymerization methods controlled by adjusting the balance of the hydrophobicity and hydrophilicity of the material. One of the solutions to control polyurethane stiffness and flexibility is to determine an appropriate balance between hydrophobicity and hydrophilicity. This may be achieved by selecting a particular type of isocyanate, polyol, chain extender, and their composition, to produce an intended combination of properties appropriate for the specific application.

It has been found that at least one novel solution to these existing problems is to make a polyurethane that has high inherent stiffness before it is exposed to in vivo condition and is able to soften more significantly than traditional polyurethane after it is in vivo condition. This solution may be achieved by making a thermoplastic polyurethane that is produced by the reaction of: an aromatic diisocyanate excluding any non-aromatic diisocyanates, at least one polyglycol, and a chain extender comprising at least one side-chain branching diol and excluding linear diols, and optionally, an amine-terminated polyether; with an isocyanate index of 1 to 1.4, and composed of the aromatic diisocyanate, the at least one polyglycol, and the at least one side-chain branching diol chain extender, and the optional amine-terminated polyether. It is also contemplated that the thermoplastic polyurethane consists essentially of the reaction product of: an aromatic diisocyanate (excluding non-aromatic diisocyanates), at least one polyglycol, and at least one side-chain branching diol chain extender (excluding linear diols), with an isocyanate index of 1 to 1.4. In various embodiments, the polyurethane may have a hard segment content between about 50% and about 75% by weight, where a hard segment is the portion(s) of the polymer molecules which include the diisocyanate and the extender components, which are generally highly crystalline due to dipole-dipole interactions and/or hydrogen bonding. In contrast, the soft segments form from the polyglycol portions between the diisocyanate of the polymer chains and generally are either amorphous or only partially crystalline due to the characteristics of the polyglycol(s).

In various embodiments, the side-chain branching diol comprises 2,2-dimethyl-1,3-propanediol, 2-methyl-1,3-propanediol, or both in a weight ratio of from 0:100 to 100:0 by weight of 2,2-dimethyl-1,3-propanediol to 2-methyl-1,3-propanediol. 2,2-dimethyl-1,3-propanediol has a greater impact on polyurethane's stiffness but less effect on tubing's softening than 2-methyl-1,3-propanediol. Therefore, the ratio by weight of 2,2-dimethyl-1,3-propanediol and 2-methyl-1,3-propanediol may be varied to provide a polyurethane product with varying properties with the same content of hard segment. In a detailed embodiment, the side-chain branching diol consists essentially of a mixture of 2,2-dimethyl-1,3-propanediol and 2-methyl-1,3-propanediol in a weight ratio of from 10:90 to 90:10.

Figure 2:
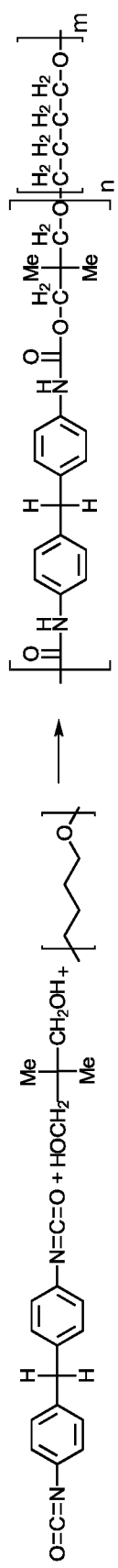
FIG. 2 illustrates an example of a polyurethane product produced by a three component reaction between an aromatic diisocyanate, a polyglycol, and a side-chain branching diol chain extender.

In one or more embodiments, the polymerization may be a one-step bulk polymerization without requiring a catalyst or other additives. An example of a polyurethane product produced by the reaction of an aromatic diisocyanate and a side-chain branching diol chain extender is illustrated in FIG. 1. This can exemplify the part of the reaction forming the hard segment including the diisocyanate and the extender components. An example of a polyurethane product produced by the three component reaction between an aromatic diisocyanate, a polyglycol, and a side-chain branching diol chain extender is illustrated in FIG. 2, where the polyglycol forms the soft segment. In various embodiments, there is no catalyst used to initiate the polymerization reaction.

In one or more embodiments, the polyurethane may be mixed with a radiopaque material, an antithrombogenic agent, an antimicrobial agent, a lubricant, a colorant, or their blends.

In various embodiments, additional materials may be added to the polyurethane polymer, for example antimicrobial agents to make antimicrobial polyurethane polymer. This antimicrobial polymer material may have a broad spectrum antimicrobial efficacy, which can provide the antimicrobial effectiveness during the polymer's shelf-life. The antimicrobial polyurethane polymer of one or more embodiments of the present invention may be used as raw material to extrude various medical devices, such as catheter tubing, an antimicrobial polyurethane sheet, or antimicrobial sponge material. These medical devices can be made with the anti-infective material that inhibits the bacterial growth in the living body during their use in clinical settings. The formed medical article may be capable of slowly releasing the anti-infective material when in contact with injectable clinically relevant solutions.

Principles and embodiments of the present invention relate to polyurethanes formulations that can overcome the aforementioned drawbacks. The stiffness and flexibility of this polyurethane, through well designed formulation, can be tailored and purposely varied, to fit different practical needs. The antimicrobial agent which may be incorporated into this polyurethane material may make the medical devices having the antimicrobial agent effective in preventing contamination. This can benefit medical workers and/or hospital patients by protective clothing and reducing disease transmissions and/or cross infections.

In one or more embodiments, the polyurethane may be composed of an aromatic diisocyanate, at least one polyglycol, and at least one side-chain branching diol chain extender. In various embodiments, the isocyanate may be selected from the group consisting of 4,4'-diphenylmethane diisocyanate (MDI) (Formula I), 2,2'-dimethyl-4,4'-biphenyldiisocyanate (Formula II), 3,3'-dimethyl-4,4'-diphenyl diisocyanate (TODI) (Formula III), 2,4-toluene diisocyanate, 2,6-toluene diisocyanate (TDI), 1,5-naphthalene diisocyanate (NDI), 4,6'-xylylene diisocyanate (XDI), 3,3'-dimethyl-diphenylmethane 4,4'-diisocyanate (DMMDI), dianisidine diisocyanate (DADI), and their blends.

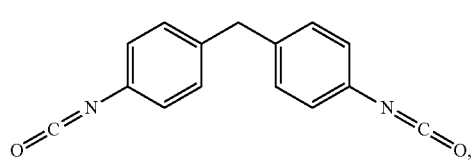

(I)

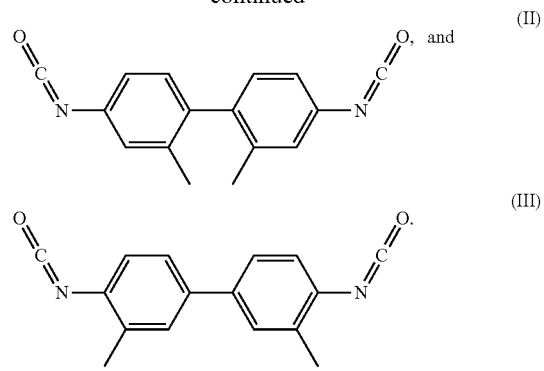

In one or more embodiments, the polyurethane has a hard segment content between 50% and 75% by weight.

In one or more embodiments, the polyglycol may be selected from the group consisting of polyethylene oxide glycol (PEG), polypropylene oxide glycol (PPG), polytetramethylene ether glycol, (PTMEG), polyester glycol, silicone glycol, polycarbonate glycol and combinations thereof. In the various embodiments, the polyglycol may be PTMEG250, PTMEG650, PTMEG1000, PTMEG1450, PTMEG1800, PTMEG2000, PTMEG2900, PEG 8000, PPG PT3000, or combinations thereof. PEG 8000 is a polyethylene glycol having a formula weight of 7,000-9,000. PPG PT3000 is a polypropylene glycol having an average molecular weight of 3,000. Desmophen® C is a polycarbonate glycol having an average molecular weight of 350 to 1000. In various embodiments, the at least one polyglycol is PTMEG having the formula: $HO(CH_2CH_2CH_2CH_2—O—)_n$ H, where n has an average value in the range of 3 to 40. In one or more embodiments, the polyols is a blend of two or more PTMEG250, PTMEG650, PTMEG1000, PTMEG1450, PTMEG1800, PTMEG2000, and PTMEG2900. In one or more embodiments, the polyols is a blend of two or more PTMEG having the formula: $HO(CH_2CH_2CH_2CH_2—O—)_nH$, where n has an average value in the range of 3 to 40.

In one or more embodiments, the polyurethane further comprises a polyetheramine. Suitable polyetheramines include but are not limited to amine-terminated polyethers having repeating units of ethylene oxide, propylene oxide or tetramethylene oxide; and having a molecular weight in the range of about 400 to 8,000. Preferred polyetheramines have propylene oxide repeating units. Jeffamine® D4000 is a specific polyetheramine, an amine-terminated polyoxypropylene glycol, having an average molecular weight of about 4000.

In one or more embodiments, the chain extenders may be selected from the group consisting of 2,2-dimethyl-1,3-propanediol, 2-methyl-1,3-propanediol, and their blends. In various embodiments, the polyurethane comprises only one side-chain branching diol as the chain extender. In various embodiments, the chain extenders exclude linear diols.

In various embodiments, a polyurethane product consisting essentially of side-chain branching diols including 2,2-dimethyl-1,3-propanediol, 2-methyl-1,3-propanediol, and their blends. In one or more embodiments, 2,2-dimethyl-1,3-propanediol and 2-methyl-1,3-propanediol are the only type of chain extender intentionally incorporated into the disclosed polyurethane formulation.

In one or more embodiments, the molecular structure of side-chain branching diols, as shown in Formula (IV), can be:

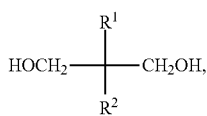

(IV)

where R¹ is a methyl group, and R² is a methyl group or hydrogen atom. In various embodiments, the mixture ratio of 2,2-dimethyl-1,3-propanediol and 2-methyl-1,3-propanediol may be from 0% to 100% by weight, or greater than 0% to less than 100%. In various embodiments, the side-chain branching diol is the only type of chain extender in the polyurethane formulation. In various embodiments, the chain extender comprises about 5% to about 20% (w/w), or about 10% to about 17% (w/w) of the polyurethane.

Aspects also relate to a melt-processable thermoplastic polyurethane comprising the reaction product of an aromatic diisocyanate selected from the group consisting of 4,4'-diphenylmethane diisocyanate, 2,2'-dimethyl-4,4'-biphenyl-diisocyanate, 3,3'-dimethyl-4,4'-biphenyl diisocyanate, and combinations thereof; at least one polyglycol selected from the group consisting of polyethylene oxide glycol (PEG), polypropylene oxide glycol (PPG), polytetramethylene ether glycol (PTMEG), polyester glycol, silicone glycol, polycarbonate glycol, and combinations thereof; and at least one chain extender selected from the group consisting of 2,2-dimethyl-1,3-propanediol, 2-methyl-1,3-propanediol, and combinations thereof.

In various embodiments, the polyurethane reaction product does not include an aminodiol chain extender. In various embodiments, the polyurethane product does not include 1,4-Butanediol (BDO), butylethyl propanediol (BEPD), bis bromomethyl propanediol (BBMPD), 1,5-pentanediol, hydroquinone bis (beta-hydroxyethyl) ether (HQEE) or their blends. In various embodiments, the polyurethane product does not include a glycol chain extender containing unsaturated carbon-carbon double bonds.

In one or more embodiments, aliphatic diisocyanates and alicyclic diisocyanates are excluded from the polyurethane product, such that the polyurethane does not comprise aliphatic diisocyanates or alicyclic diisocyanates.

The polyurethanes described herein may be fabricated into film, tubing, and other forms by conventional thermoplastic fabricating techniques including melt casting, extrusion, molding, etc. The polyurethane described herein may be used for PICCs and CVCs. The polymer may have incorporated therein, as desired, conventional stabilizers and radiopaque materials such as barium sulfate and the like. The amounts of these materials will vary depending upon the application of the polyurethane, but they are typically present in amounts so ranging from 0.1 to 40 weight percent of the polymer.

Aspects of the present invention also relate to a vascular access device comprising the melt-processable thermoplastic polyurethane described herein. The vascular access device may be selected from a group including a central venous catheter, a peripherally inserted central catheter, or peripheral intravenous cannula.

The stiffness, flexibility and polyurethane's softening are dependent of its molecular structure and its environment. Polyurethane's flexibility can be changed by a change of its environment, and controlled by adjusting the balance of its hydrophobicity and hydrophilicity of the material. The hydrophobicity and hydrophilicity depends on its molecular structure and composition.

General Procedure for Polyurethane Synthesis

The polyurethanes discussed here were prepared by "one shot" bulk polymerization process. The polyol(s) and chain extender(s) were mixed thoroughly with vacuum stripping first and then with nitrogen gas purging for 12 to 24 hours. At ambient temperature, the calculated quantity of MDI was added all at once with very vigorous stirring. Vigorous stirring was conducted, then the mixture was poured into a Teflon-lined tray and immediately placed in an oven for post curing.

Exemplary Formulations with the proviso that the ingredients total 100%.

| Reactant | A by weight | B by weight | C by weight |
|---|---|---|---|
| Aromatic Diisocyanate | 40.0-55.0% | 45.0-50.0% | 46.0-49.0% |
| Total Polyglycol | 15-59.9% | 20-54.9 | 25-49.9 |
| PTMEG Nominal 250 ≥ MW < 1000 daltons | 10-35% | 13-32% | 14-28% |
| PTMEG Nominal 1000 ≥ MW ≤ 2900 daltons | 5-50% | 7-35% | 15-25% |
| PEG MW 400-8000 | 0-50% | 0-40% | 0-35% |
| Polyetheramine MW230-4000 | 0-30% | 0-25% | 0-20% |
| Branched diol chain extender | 0.1-25% | 5-20% | 12-18% |
| Hard Segment % | 50-75% | 52-68% | 60-65% |

EXAMPLES

Inventive Example 1

A polyurethane was made by the "one shot" bulk polymerization process (no catalyst) in accordance with Exemplary Formulation C as shown above using MDI as the aromatic diisocyanate with and the polyglycol PTMEG of varying molecular weights (Nominal MW<1000 and Nominal 1000≥MW≤2900). The chain extender was 2,2-dimethyl-1,3-propanediol.

Example 2

Reference

A reference polyurethane was made by the "one shot" bulk polymerization process (no catalyst). The reference polyurethane utilized MDI as the aromatic diisocyanate and the polyglycol PTMEG with a narrower PTMEG molecular weight distribution relative to Inventive Example 1. The reference polyurethane uses a linear diol as a chain extender.

Example 3

Testing

The polyurethanes of Inventive Example 1 and Reference Example 2 were tested for tensile strength and elongation. The tensile, elongation and modulus of the polyurethane of the invention may be measured by ASTM procedure D638 using an Instron Universal Testing Instrument, Model 1122. Table 1 provides the comparison of results.

TABLE 1

| | Inventive Example 1 | Reference Example 2 |
|---|---|---|
| Tensile Strength at 5% Elongation at RT (psi) | 3718 | 2105 |
| Tensile Strength at 25% Elongation at RT (psi) | 2583 | 2225 |

TABLE 1-continued

|  | Inventive Example 1 | Reference Example 2 |
|---|---|---|
| Tensile Strength at 50% Elongation at RT (psi) | 2669 | 2573 |
| Tensile Strength at 100% Elongation at RT (psi) | 3556 | 3122 |
| Tensile Strength at 200% Elongation at RT (psi) | 6669 | 5273 |
| Tensile Strength at Break (psi) | 10014 | 10623 |
| Elongation at break at RT (%) | 283 | 249 |

Table 2 shows the comparisons of material stiffness of a reference polyurethane and an inventive polyurethane formulation of Example 1 before and after soaking in 37° C. normal saline solution. The 37° C. normal saline solution is used to simulate the body environment that catheter tubing is typically exposed to in the vein. An 18 gauge single-lumen tubing made from the inventive polyurethane formulation of Example 1 had a higher bend force (118 g) before soaking in 37° C. normal saline solution relative to an 18 gauge single-lumen tubing made from Reference Example 2 (45 g), which means the inventive polyurethane is initially stiffer (2.6 times). However, after being soaked in 37° C. normal saline solution for 24 hours, the inventive polyurethane formulation exhibited a lower stiffness (bend force of 21.9) than the reference example (bend force of 29.3 g). Regarding flexibility, the inventive polyurethane exhibited a larger softening ratio (81.5%) compared to the reference polyurethane (35%). One potential application of one or more embodiments of the inventive polyurethane formulation is as a catheter tubing material. The polyurethane formulation of one or more embodiments of the present invention has a higher stiffness before soaking which is able to significantly improve the ease of catheter stick, threading and first-stick success of catheter tubing. Meanwhile, polyurethane formulation of one or more embodiments of the present invention has a higher flexibility after soaking allowing catheter tubing, made from this polyurethane, after being placed in patient's vein, can provide the patient with greater comfort and less catheter tubing-related complications. Additionally, the polyurethane formulation of one or more embodiments of the present invention can achieve a greater stiffness than the comparative polyurethane at the same content of hard segment. Lower hard segment will be helpful to increase processability of polyurethane and reduce its aging or sterilization induced material yellowing.

A comparison of the stiffness of 18 gauge single-lumen tubing made from the comparative Reference Example 2 polyurethane and Inventive Example 1 is shown in Table 2.

TABLE 2

|  | Inventive Example 1 | Reference Example 2 |
|---|---|---|
| Bend force at ambient condition* (gram force) | 118 | 45 |
| Bend force after 2 hr soaking in 37° C. normal saline solution (gram force) | 21.9 | 29.3 |
| Degree of softening | 81.5% | 35% |

*Ambient condition: 23° C. and 50% relative humidity.

Polyurethane Compounding and Single-Layer Tubing Extrusion

The synthesized polyurethane slab was ground into granulates by a Foremost grinder. The granulate of polyurethane was compounded into uniform sized polyurethane pellet by a twin-screw compounder. The compounding condition was given in Table 3. The compounded pellets were dried for 24 hours and extruded into 18 gauge tubing with Davis-Standard single screw extruder.

TABLE 3

| Compounding Condition | Inventive Example 1 |
|---|---|
| TEMP, ° F., Zone 1 | 400° F. |
| Zone 2 | 410° F. |
| Zone 3 | 420° F. |
| Zone 4 | 450° F. |
| Zone 5 | 460° F. |
| Screw RPM | 225 |

The extrusion conditions were given in Table 4.

TABLE 4

| Controlled Zone | Temperature |
|---|---|
| TEMP, ° F., Zone 1 | 410° F. |
| Zone 2 | 435° F. |
| Zone 3 | 460° F. |
| Head Clamp | 450° F. |
| Melt Pump | 445° F. |
| Outlet | 440° F. |
| Adapter | 440° F. |
| Die 1 | 435° F. |
| Die 2 | 435° F. |

Table 5 shows a comparison of physical properties of 18 gauge tubing made from a reference polyurethane synthesized from traditional linear diols to the inventive polyurethane formulation of Example 1 before and after soaking in 37° C. normal saline solution for 2 hours to simulated a body environment. As discussed with respect to Table 2, an 18 gauge single-lumen tubing made from the inventive polyurethane formulation had a higher bending force (118 g) before soaking in 37° C. normal saline solution relative to an 18 gauge single-lumen tubing made from Reference Example 2 (45 g), which means the inventive polyurethane is intrinsically stiffer. The inventive polyurethane has almost identical hard segment content as the Reference Example polyurethane does. The advantage of the inventive polyurethane is that it is able to achieve a much higher stiffness, without the need to increase its content of hard segment, unlike what traditional polyurethane requires. The potential application of the inventive polyurethane formulation is to replace FEP-based IV catheter tubing material, which has high initial stiffness before the catheter tubing's insertion, but softens very little after insertion.

The stiffness, flexibility and polyurethane's softening are dependent of its molecular structure and its environment. Polyurethane's stiffness can be changed by a change of its environment, and controlled by adjusting the balance of its hydrophobicity and hydrophilicity of the material. This depends on its molecular structure and composition.

Table 5 shows a comparison of bending resistance of an 18 gauge tube under different environmental conditions between the comparative Reference Example polyurethane and the inventive polyurethane.

TABLE 5

|  | Inventive Example 1 | Reference Example 2 |
|---|---|---|
| Bend force at ambient condition (gram force) | 118 | 45 |
| Bend force after 40 h exposure in Climate Zone IV condition - 30° C., 70% Relative Humidity. (gram force) | 99 | 40 |

Table 5 shows the impact of different environmental condition on the tubing stiffness. The condition of 30° C. and 70% relative humidity represents the environmental condition of hot and humid Climate Zone IV areas in the world (Ref: USP <1151> Climatic Conditions). Table 5 indicates that the inventive polyurethane material is still able to maintain much higher stiffness under the Climate zone IV condition than the comparative Reference Example.

Determination of Bend Force and Percent Softening

Stiffness of the catheter tubing was characterized by maximum bend force measurements. Bend force testing was performed on two inch lengths of catheter tubing with an Instron Universal Testing Machine, Model 1122 equipped with a 2000 g load cell. Compression measurement of maximum axial force required to bend the tubing was taken. Degree of tubing softening was determined by the percent of bend force reduction measured after the tubing was conditioned for at least 40 hours at 25° C. and 24 hours in 37° C. normal saline solution.

Polyurethane Compounding and Striped or Laminated Tubing Extrusion

In a similar way as described in above, besides pure polyurethane pellet, the granulate of polyurethane was also compounded with barium sulfate powder to form a radio opaque polyurethane-barium sulfate blend by traditional conventional compounding machines.

The compounded pellets were dried for 24 hours and extruded into 18 gauge six-stripe catheter tubing with Davis-Standard coextruder. The base polymer melt stream of virgin polyurethane from the primary extruder and a polymer melt stream containing the aforementioned compound of the polyurethane and barium sulfate agent from the secondary extruder were maintained separately until combined as continuous layers in the forward, down stream portion of an extruder head. From the extruder head, the streams subsequently passed through and emerged from a tube die (coaxial or cross-head) as an integral tubing member. The encapsulated six stripes were made from the compound of the blend of polyurethane and barium sulfate and the rest of part of the tubing was made from pure polyurethane only.

The extrusion conditions were given in Table 6.

TABLE 6

| Extrusion Conditions of Primary Extruder | Polymer Melt | Extrusion Conditions of Secondary Extruder | Polymer Melt |
|---|---|---|---|
| TEMP, ° F., Zone 1 | 412° F. | TEMP, ° F., Zone 1 | 350° F. |
| Zone 2 | 418° F. | Zone 2 | 353° F. |
| Zone 3 | 430° F. | Zone 3 | 358° F. |
| Head Clamp | 425° F. | Head Clamp | 360° F. |
| Melt Pump | 425° F. | Melt Pump | 362° F. |
| Outlet | 426° F. | Outlet | 364° F. |
| Adapter | 426° F. | Adapter | 365° F. |

TABLE 6-continued

| Extrusion Conditions of Primary Extruder | Polymer Melt | Extrusion Conditions of Secondary Extruder | Polymer Melt |
|---|---|---|---|
| Die 1 |  |  | 427° F. |
| Die 2 |  |  | 427° F. |

Embodiments of catheter tubing based on polyurethanes discussed herein can be varied by changing and proper selecting of extruder/coextruders, extrusion dies, the number of stripes and layers, the volume percentage of stripe material and the type of radiopaque agent.

In various embodiments commercially available antimicrobial agents that are highly effective to prevent the bacterial growth may be incorporated into the polyurethane. The antimicrobial agents may be selected from the group consisting of chlorhexidine diacetate, Triclosan, benzalkonium chloride, para-chlorometa-xylenol and combinations thereof, which have been shown to inhibit bacterial growth. Particularly chlorhexidine diacetate has broad spectrum anti-infective properties and has been widely used in medical applications. Triclosan, on the other hand, is widely used in the manufacture of consumer products to inhibit bacterial growth. It is generally known that triclosan is a stable antimicrobial agent that melts around 560° C.

Chlorhexidine diacetate has a melting range of 153° C. to 157° C., and is relatively stable at or below 190° C. In various embodiments, a combination of the polyurethane polymers with triclosan or chlorhexidine diacetate or both may be blended within the preferred temperatures to extrude or mold a desired medical article.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A melt-processable thermoplastic polyurethane comprising the reaction product of the following ingredients:
   46 to 49% by weight of an aromatic diisocyanate that is 4,4'-diphenylmethane diisocyanate;
   14 to 28% by weight of a first polytetramethylene ether glycol (PTMEG) having a first nominal molecular weight in the range of 250 to less than 1000 daltons;

15 to 25% by weight of a second PTMEG having a second nominal molecular weight in the range of 1000 to 2900 daltons; and 12 to 18% by weight of a chain extender consisting of: 2,2-dimethyl-1,3-propanediol;

with the proviso that amounts of the aromatic diisocyanate, the first and second PTMEGs, and the chain extender add to 100%;

wherein the hard segment content is in a range of 60 to 65% and when the thermoplastic polyurethane is melt-processed to form 18-gauge tubing, the thermoplastic polyurethane is effective to exhibit a degree of softening of 81.5% going from an ambient condition of 23° C. and 50% relative humidity for 24 hours to a simulated body environment of 37° C. in saline solution for 24 hours.

2. The melt-processable thermoplastic polyurethane of claim 1, which further comprises one or more of a radiopaque material, an antithrombogenic agent, an antimicrobial agent, a lubricant, or a colorant.

3. A vascular access device comprising the melt-processable thermoplastic polyurethane of claim 1.

4. The vascular access device of claim 3, wherein the vascular access device is selected from the group consisting of: a central venous catheter, a peripherally inserted central catheter, or peripheral intravenous cannula.

5. A method of making a vascular access device comprising:

obtaining the melt-processable thermoplastic polyurethane of claim 1 by polymerizing the ingredients in a one-step bulk polymerization without a catalyst;

curing the polyurethane;

convening the polyurethane into chips; and melt forming the polyurethane into vascular access devices.

* * * * *